United States Patent [19]
Carson et al.

[11] Patent Number: 5,409,902
[45] Date of Patent: * Apr. 25, 1995

[54] ORAL HYGIENE COMPOSITIONS CONTAINING GLYCEROGLYCOLIPIDS AS ANTIPLAQUE COMPOUNDS

[75] Inventors: Robert G. Carson, Rahway, N.J.; Anthony Hung, New City, N.Y.; Kurt M. Schilling, Verona; Shang-Ren Wu, Mahwah, both of N.J.

[73] Assignee: Lever Brothers Company, New York, N.Y.

[ * ] Notice: The portion of the term of this patent subsequent to Jan. 31, 2012 has been disclaimed.

[21] Appl. No.: 816,418

[22] Filed: Dec. 31, 1991

[51] Int. Cl.$^6$ ............................................. A61K 7/16
[52] U.S. Cl. ................................ 514/23; 252/174.17; 424/49; 424/52; 424/57; 514/25; 514/901
[58] Field of Search ............... 424/49, 52, 57; 514/23, 514/25, 901; 252/174.17

[56] References Cited

U.S. PATENT DOCUMENTS

| | | | |
|---|---|---|---|
| 3,988,482 | 10/1976 | Higashiyama et al. | 426/48 |
| 4,663,202 | 5/1987 | Causton | 424/49 |
| 4,665,060 | 5/1987 | Mardh et al. | 514/54 |
| 4,675,392 | 6/1987 | Dahmen et al. | 536/17.6 |
| 4,724,205 | 2/1988 | Karlsson et al. | 435/34 |
| 4,851,338 | 7/1989 | Mardh et al. | 514/54 |
| 4,855,128 | 8/1989 | Lynch et al. | 424/49 |
| 4,868,289 | 9/1989 | Magnusson et al. | 536/4.1 |
| 4,877,603 | 10/1989 | Degenhardt et al. | 424/57 |
| 4,920,100 | 4/1990 | Lehmann et al. | 424/49 |
| 4,992,420 | 2/1991 | Neeser | 514/775 |
| 4,994,441 | 2/1991 | Neeser | 514/775 |
| 5,002,759 | 3/1991 | Gaffar et al. | 424/441 |
| 5,071,977 | 12/1991 | Cassels et al. | 536/123 |
| 5,116,821 | 5/1992 | Randall et al. | 514/53 |
| 5,145,665 | 9/1992 | Klueppel et al. | 424/49 |

FOREIGN PATENT DOCUMENTS

| | | |
|---|---|---|
| 0285178 | 10/1988 | European Pat. Off. |
| 71635 | 1/1975 | Luxembourg |
| 2021949 | 12/1979 | United Kingdom |
| 2224204 | 5/1990 | United Kingdom |
| 90/01488 | 2/1990 | WIPO |
| WO92/06692 | 4/1992 | WIPO |

OTHER PUBLICATIONS

Gibbons, R. J. "Bacterial Adhesion to Oral Tissues: A Model for Infectious Diseases." Journal of Dental Research, vol. 68, No. 5, (May 1989), pp. 750–760.

Kolenbrander, Paul E., "Surface Recognition among Oral Bacteria: Multigeneric Coaggregations and Their Mediators." Critical Reviews in Microbiology, vol. 17, Issue 2 (1989), pp. 137–159.

Stromberg, Nicklas et al., "Characterization of the Binding of Actinomyces naeslundii (ATCC 12104) and actinomyces viscosus (ATCC 19246) to Glycosphingolipids, Using a Solid–phase Overlay Approach." The Journal of Biological Chemistry, vol. 265, No. 19, (Jul. 5, 1990), pp. 11251–11258.

Stromberg, Nicklas et al., Abstracts of International Association for Dental Research Scandinavian Division, Helsinki, Abstract No. 10, Aug. 22–24, 1991.

Stromberg, Nicklas et al., Abstracts of International Association for Dental Research Scandinavian Division, Helsinki, Abstract 12, Aug. 22–24, 1991.

McIntire, Floyd C. et al., "Structural Preferences of $\beta$-Galactoside–Reactive Lectins on Actinomyces viscosus T14V and Actinomyces naeslundii WVU45." Infection and Immunity, vol. 41, No. 2 (Aug. 1983), pp. 848–850.

(List continued on next page.)

Primary Examiner—Ronald W. Griffin
Attorney, Agent, or Firm—Rimma Mitelman

[57] ABSTRACT

Oral hygiene antiplaque compositions which include as an active ingredient a glyceroglycolipid having an amine or ether linkage and containing a $\beta$-D-galactose moiety (a sugar moiety recognized by lectins on oral bacteria). The compositions containing glyceroglycolipids provide enhanced inhibition of bacterial adhesive interactions and may provide a surfactancy benefit and/or antibacterial benefit.

16 Claims, No Drawings

OTHER PUBLICATIONS

Nilsson, Kurt G. I., "A Simple Strategy for Changing the Regioselectivity of Glycosidase-catalysed Formation of Disaccharides: Part II, Enzymic Synthesis in situ of Various Acceptor Glycosides." Carbohydrate Research, vol. 180 (1988) pp. 53–59.

Lee, Reiko T., et al., "Synthesis of 3-(2-Aminoethylthio) Propyl Glycosides" Carbohydrate Research, vol. 37 (1974), pp. 193–201.

Iranpoor N., et al., "2,3-Dichloro-5,-6-Dicyano-P-Benzoquinone, an Efficient, Mild, Neutral and Highly Regioselective Catalyst for Alcoholysis of Epoxides", Tetrahedron Letters, vol. 31, No. 5, (1990), pp. 735–738.

Collins, Peter M., et al. "Preparation of 3-Methoxycar-bonylpropyl-α-D and 7-Methoxycarbonylhexyl β-D-Galacto-pyranosides: Space-arm Glycosides for Branched Oligosaccharide Synthesis". J. Chem. Soc. Perkin Trans. (1984), pp. 1525–1530.

Abstract of Japanese Patent Application 5,507,6811.

Abstract of European Patent Application 184,121.

Matsumura et al., *JAOCS*, vol. 67, No. 12, Dec. 1990, pp. 996–1001.

Leon-Ruaud et al., *Tetrahedron*, vol. 47, No. 28, pp. 5185–5192, (1991).

Abstract of U.S. Ser. No. 07/516,463.

Abstract of U.S. Ser. No. 07/071,977.

European Search Report EP 92 20 3971.

Patent Abstracts of Japan, vol. 13, No. 273 (C-609) (3621), JP 167237.

Calderone, Richard A. et al., "Adherence and Receptor Relationships of *Candida albicans*", Microbiological Reviews, vol. 55, No. 1, Mar. 1991, pp. 1–20.

ORAL HYGIENE COMPOSITIONS CONTAINING GLYCEROGLYCOLIPIDS AS ANTIPLAQUE COMPOUNDS

FIELD OF THE INVENTION

The invention relates to oral hygiene compositions which inhibit aggregation of bacteria responsible for dental plaque.

BACKGROUND OF THE INVENTION

The inventive compositions include antiplaque agents which are glyceroglycolipids containing at least one $\beta$-D-galactose group having a structure shown below.

Natural glycolipids are known in the art and these structures have been elucidated. The term glycolipid refers to any of a class of lipids that, upon hydrolysis, yield a sugar (e.g., galactose or glucose), and a lipid (e.g. substituted glycerol group). One major class of these glycolipids belong to the glycero glycolipids, i.e., a glycolipid based around a glycerol frame structure. For example, the compound may have a sugar structure at one end of the glycerol structure instead of an —OH group and an ester linkage at one or both of the other —OH groups that would normally be found on glycerol. Another example of a glyceroglycolipid is a compound having a sugar structure at one end of a glycerol structure instead of an —OH group and ether linkage on one or both of the other —OH groups that would normally be found on glycerol.

Yet another example of a glyceroglycolipid might be a compound with a sugar group on one end of the glycerol structure instead of an —OH group and an amine group (i.e., $NRR^1$) at one or both of the other —OH groups normally found in glycerol, and in particular amines wherein one or both of R and $R^1$ are alkyl chains.

Concurrently filed commonly assigned applications Ser. No. 07/816,423 and Ser. No. 07/816,4 both now abandoned disclose the general utility of glyceroglycolipids having an amine and an ether linkage as surfactants in personal products and detergent formulations. Oral hygiene compositions according to the present invention may include surfactant molecules taught by the concurrently filed application, but the present invention is based, in part, on the discovery that glyceroglycolipids containing a $\beta$-D-galactose group and having specific structures described in a greater detail below provide an antiplaque benefit by disrupting stereospecific bacterial binding.

It is generally recognized that the development of dental plaque begins with the adhesion of bacteria to the teeth. Bacterial adhesion to tooth surfaces usually involves stereospecific interactions between cell surface binding proteins, referred to as adhesins, and cognate structures which form binding sites either in salivary pellicle, or on the surfaces of other bacteria resident in plaque, or in the extracellular plaque matrix (Gibbons, R. J.; J Dent Res 68,750–760).

Many of the oral bacterial adhesins described in the art exhibit carbohydrate-specific binding and are often found on filamentous extensions (i.e., pili or fimbriae) which protrude from cell surfaces. These carbohydrate recognition structures, which are also referred to as lectins, mediate binding to host-derived or microbial-derived saccharide-containing structures on the teeth. Several different bacterial lectins have been described in the literature. By far, the lectins most commonly expressed by plaque bacteria are $\beta$-galactoside-specific or "lactose sensitive" adhesins. The genera of bacteria which produce $\beta$-galactoside-specific adhesins cover a diverse taxonomic range, including Actinomyces, Streptococcu, Porphyromonas, Fusobacterium, Haemophilus, Capnocytophaga, Veillonella, Prevotella, Staphylococcus, and Neisseria; these represent both primary and secondary colonizers of the teeth (Kollenbrander, P. E.; Crit Rev Microbiol 17:137–159). Kollenbrander notes that bacterial coaggregation plays an active role in formation of dental plaque on the teeth and adherence of bacteria to epithelial cells in the oral econiche.

Most attempts to control plaque through anti-adhesion mechanisms have involved non-stereospecific inhibition of bacterial attachment to the teeth, usually with compositions containing surface-active polymers. For instance, G.B. Pat. No. 2,224,204A and U.S. Pat. No. 4,877,603 disclose oral compositions which include phosphonate-containing polymers that inhibit bacterial attachment to hydroxyapatite surfaces. Similarly, U.S. Pat. No. 4,663,202 discloses a method for treating surfaces with combinations of polymers which form barriers that retard bacterial adsorption.

With respect to blocking stereospecific interactions which mediate oral bacterial adherence, the use of mono- and oligosaccharides has been described, as inhibitors of lectin-mediated adhesion to human cells. For instance, U.S. Pat. No. 5,071,977 describes oligosaccharides isolated from S. sanguis, which inhibit the build-up of adhesive dental plaque. Gaffar et al. (U.S. Pat. No. 5,002,759) disclose oligosaccharides containing either a galactose moiety (which may be $\beta$-D-galactose and/or a fucose moiety as agents in dentifrice preparations for inhibiting adherence of Streptococcus pyogenes to human epithelial cells. European Patent Application 184,121 discloses the use of galactose and/or lactose as anti-caries agents in foods, drinks, and pharmaceutical preparations. Neeser (U.S. Pat. Nos. 4,992,420 and 4,994,441) describes kappa-caseino-glycopeptide compounds and desialylated derivatives thereof (the derivatives contain $\beta$-D-galactose groups) as inhibitors of in vitro adhesion by dental plaque bacteria to human erythrocytes.

Lynch et al. (U.S. Pat. No. 4,855,128) disclose polysaccharides such as xanthan gum, gum tragacanth, guar gum, gum karaya, chondroitin sulfate, polygalacturonic acid (pectin), sodium alginate and carrageenans of the kappa/lambda configuration as plaque-inhibitory agents which inhibit bacterial coaggregation; carrageenans of kappa/lambda configuration and chondroitin sulfate contain $\beta$-D-galactose.

Stromberg et al. (J. Biol. Chem. 265,11251–11258) disclose that N-acetyl-galactosamine-$\beta$1,3-galactose-O-ethyl (a $\beta$-galactosamine glycoside) is an inhibitor of binding by Actinomyces viscosus and Actinomyces naeslundii to human erythrocytes. McIntire et al. (Infection and Immunity, vol. 41, No. 2, 848–850) have described O-glycosides of galactose-$\beta$1,3-N-acetyl-galactosamine, including phenyl, phenylethyl, and nitrophenyl derivatives, which inhibit coaggregation between Actinomyces sp. and Streptococcus sanguis; McIntire et al. note that the addition of aglycones increased the inhibitory activity significantly but not greatly.

Stromberg et al. ("Synthetic Receptoranalogues Prevent Plaque Formation in Man", Abstracts of International Association for Dental Research Scandinavian Division, Helsinki, Aug. 22-24 1991) disclose a study demonstrating the plaque inhibitory activity of GalNAcβ-3Galα1-O-ethyl, which blocked adherence of Actinomyces strains 12104 and LY7. Clinical plaque strains were evaluated in a mouth rinse experiment including five human individuals. The study is said to demonstrate that receptor analogues such as GalNAcβ-3Galα1-O-ethyl, may prove useful in future antiplaque therapy. However, glycosides made from disaccharides such as disaccharides disclosed by the Stromberg and McIntire references are expensive molecules to synthesise; hence, their practical utility is limited to the study of stereospecifity of bacterial binding.

Lectin binding site analogues derived from saccharides but distinct from the compounds employed in the present invention have been disclosed for applications in a non-dental environment. Mardh et al. (U.S. Pat. No. 4,851,338) disclose the use of glycosides of structure 1 (which may contain β-D-galactose) for diagnosing the presence of Staphylococcus bacteria and bacteria from the genus *Bordatella pertussis*.

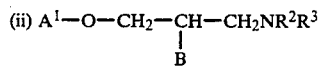

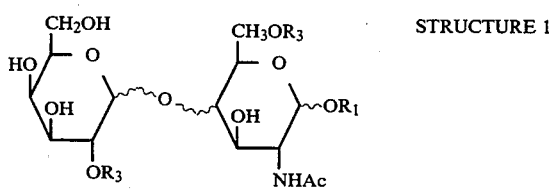

Wherein $R_1$, $R_2$, and $R_3$ are same or different and are hydrogen or an organic residue, for example lower alkyl, lower acyl, or a carbohydrate residue or an inorganic residue, such as sulphate or phosphate, and wherein $OR_1$ is an α- or β- configuration.

Dental art heretofore has not made available a dentifrice composition containing relatively cost-effective synthetic glyceroglycolipid antiplaque agents which are capable of inhibiting bacterial adhesive interactions.

Accordingly, it is an object of the present invention to provide oral hygiene compositions which include glyceroglycolipids as antiplaque agents.

It is another object of the invention to provide methods of inhibiting bacterial adhesion in the oral cavity.

These and other objects of the invention will become more apparent from the detailed description and examples that follow.

SUMMARY OF THE INVENTION

The above objects are accomplished by the present invention which includes oral hygiene compositions containing:

an effective antiplaque amount of at least one compound selected from the group consisting of:

(i) $A^1-O-CH_2-\underset{\underset{OR^1}{|}}{CH}-CH_2OR$  FORMULA A

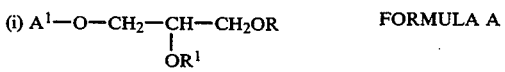

wherein $A^1$ is a saccharide comprising β-D-galactose and wherein R and $R^1$ are the same or different and are selected from the group consisting of hydrogen, an aliphatic hydrocarbon radical, an aromatic radical, a cycloaliphatic radical, and an acyl group, except that R and $R^1$ cannot both be hydrogen at the same time; and (ii) $A^1-O-CH_2-\underset{\underset{B}{|}}{CH}-CH_2NR^2R^3$  FORMULA B wherein $R^2$ and $R^3$ are the same or different and are selected from the group consisting of hydrogen, an aliphatic hydrocarbon radical, an aromatic radical, and a cycloaliphatic radical and wherein B is OH or a $NR^5R^6$ group wherein $R^5$ and $R^6$ may be the same or different and are hydrogen, an aliphatic hydrocarbon radical, an aromatic radical, and a cycloaliphatic radical, wherein B and $NR^2R^3$ are positionally interchangeable, and wherein preferably at least one of $R^2$, $R^3$, $R^5$, or $R^6$ must be a hydrocarbon radical having from 1 to 36 carbon atoms; and Compounds of Formulae A and B represent glyceroglycolipids which may be suitably employed according to the invention as antiplaque agents in oral hygiene compositions.

As long as the requirement for the presence of at least one β-galactose group is satisfied, A1 may be a mono-, di-, or oligosaccharide. Preferably, in order to simplify synthesis and reduce cost A1 is a disaccharide (e.g., lactose) or β-galactose.

The inventive dental compositions incorporate glyceroglycolipids which provide enhanced inhibition of bacterial adhesive interactions. Certain glyceroglycolipids within the scope of the invention are capable of providing a surfactancy benefit and/or anti-bacterial benefits in addition to inhibiting bacterial adhesive interactions. Such dual or triple action glyceroglycolipids are preferred antiplaque agents according to the invention, due to their ability to inhibit bacterial adhesive interactions and disperse bacteria and/or provide antibacterial activity at the same time.

The inventive compositions inhibit adhesion and/or growth of bacteria responsible for dental plaque, thereby preventing the plaque formation, plaque-induced diseases, calculus formation, dental caries, gingivitis, and periodontal disease.

The compositions of the present invention may be in the form of toothpastes, mouthwashes, rinses, tooth powders, gels, dental flosses, chewing gums, and lozenges, as well as other oral delivery vehicles.

The invention also includes methods of inhibiting plaque formation and growth which include applying the inventive compositions into the oral cavity.

DETAILED DESCRIPTION OF THE INVENTION

Oral hygiene compositions of the invention include an effective antiplaque amount of at least one glyceroglycolipid compound containing a β-galactose group and having a structure as discussed below.

In the first embodiment of the invention, the inventive compositions include an effective antiplaque amount of a glyceroglycolipid of Formula A:

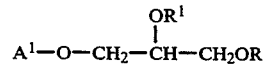

wherein $A^1$ is a saccharide, preferably β-D-galactose or disaccharide (i.e., lactose), and R and $R^1$ are the same or different and are selected from the group consisting of hydrogen, an aliphatic hydrocarbon radical, an aromatic radical, a cycloaliphatic radical, and an acyl group, except that R and R¹ cannot both be hydrogen at the same time. R and R¹ preferably contain up to 36 carbon atoms total, mosty preferably from 6 to 18 carbon atoms to deliver the additional surfactancy benefit. Most preferably, R¹ is hydrogen and R is an aliphatic hydrocarbon radical containing 6 to 18 carbon atoms.

Suitable aliphatic hydrocarbon radicals include saturated and unsaturated radicals including but not limited to methyl, ethyl, amyl, hexyl, heptyl, nonyl, decyl, undecyl, dodecyl, tridecyl, tetradecyl, pentadecyl, hexadecyl, heptadecyl, and octadecyl, and allyl, undecenyl, oleyl, linoleyl, linolenyl, propenyl, and heptenyl. The active compounds of the inventive compositions may contain straight or branched aliphatic groups. Aromatic radicals are exemplified by phenyl or substituted phenyl groups. Suitable mixed aliphatic aromatic radicals are exemplified by benzyl, phenyl ethyl, phenoxy ethyl, and vinyl benzyl. Cycloaliphatic radicals are exemplified by but not limited to cyclopentyl and cyclohexyl.

Examples of compounds suitable for inclusion in the inventive compositions according to the first embodiment of the invention are set forth below:

3-(butyloxy)-2-hydroxypropyl-$\beta$-D-Galactopyranoside
3-(pentyloxy)-2-hydroxypropyl-$\beta$-D-Galactopyranoside
3-(hexyloxy)-2-hydroxypropyl-$\beta$-D-Galactopyranoside
3-(heptyloxy)-2-hydroxypropyl-$\beta$-D-Galactopyranoside
3-(octyloxy)-2-hydroxypropyl-$\beta$-D-Galactopyranoside
3-(nonyloxy)-2-hydroxypropyl-$\beta$-D-Galactopyranoside
3-(decyloxy)-2-hydroxypropyl-$\beta$-D-Galactopyranoside
3-(dodecyloxy)-2-hydroxypropyl-$\beta$-D-Galactopyranoside
3-(tetradecyloxy)-2-hydroxypropyl-$\beta$-D-Galactopyranoside
3-(hexadecyloxy)-2-hydroxypropyl-$\beta$-D-Galactopyranoside
3-(octadecyloxy)-2-hydroxypropyl-$\beta$-D-Galactopyranoside
3-(eicosyloxy)-2-hydroxypropyl-$\beta$-D-Galactopyranoside
3-(docosyloxy)-2-hydroxypropyl-$\beta$-D-Galactopyranoside
3-(tetracosyloxy)-2-hydroxypropyl-$\beta$-D-Galactopyranoside
3-(hexenyloxy)-2-hydroxypropyl-$\beta$-D-Galactopyranoside
3-(decenyloxy)-2-hydroxypropyl-$\beta$-D-Galactopyranoside
3-(dodecenyloxy)-2-hydroxypropyl-$\beta$-D-Galactopyranoside
3-(tetradecenyloxy)-2-hydroxypropyl-$\beta$-D-Galactopyranoside
3-(hexadecenyloxy)-2-hydroxypropyl-$\beta$-D-Galactopyranoside
3-(octadecenyloxy)-2-hydroxypropyl-$\beta$-D-Galactopyranoside
3-(docosenyloxy)-2-hydroxypropyl-$\beta$-D-Galactopyranoside
3-(tetracosenyloxy)-2-hydroxypropyl-$\beta$-D-Galactopyranoside
3-(3-oxa-tridecyloxy)-2-hydroxypropyl-$\beta$-D-Galactopyranoside
3-(fluorododecyloxy)-2-hydroxypropyl-$\beta$-D-Galactopyranoside
3-(octyloxy)-2-hydroxypropyl-$\beta$-lactoside
3-(dodecyloxy)-2-hydroxypropyl-$\beta$-lactoside
3-(dodecyloxy)-2-hydroxypropyl-$\alpha$-lactoside In the second embodiment of the invention, the inventive compositions include an effective antiplaque amount of a glyceroglycolipid of Formula B $$A^1-O-CH_2-\underset{\underset{B}{|}}{CH}-CH_2NR^2R^3$$

wherein $A^1$ is a saccharide, preferably $\beta$-D-galactose or disaccharide (i.e., lactose), $R^2$ and $R^3$ are the same or different and are selected from the group consisting of hydrogen, an aliphatic hydrocarbon radical, an aromatic radical, and a cycloaliphatic radical and wherein B is OH or a $NR^5R^6$ group wherein $R^5$ and $R^6$ may be the same or different and are hydrogen, an aliphatic hydrocarbon radical, an aromatic radical, and a cycloaliphatic radical, wherein B and $NR^2R^3$ are positionally interchangeable.

Preferably, at least one of $R^2$, $R^3$, $R^5$ or $R^6$ is a hydrocarbon radical (i.e., not all are hydrogen at the same time) in order to attain surfactancy benefit in addition to bacterial antiadhesion benefit. Preferably, at least one of these groups should be $C_6$–$C_{22}$, more preferably $C_6$–$C_{18}$, most preferably $C_{10}$–$C_{14}$.

Preferably, again in order to maximize the surfactancy benefit, the Formula B compound is a monoalkylamine such that $R^2$ (or $R^3$) is hydrogen and $R^3$ (or $R^2$) is an alkyl chain having, for example, 10 to 14 carbons.

Most preferably, $A^1$ is $\beta$-galactose, $R^2$ is a $C_6$–$C_{18}$ alkyl chain, $R^3$ is hydrogen and B is OH, to reduce cost and to attain surfactancy benefit.

Suitable aliphatic hydrocarbon radicals include saturated and unsaturated radicals including but not limited to methyl, ethyl, amyl, hexyl, heptyl, nonyl, decyl, undecyl, dodecyl, tridecyl, tetradecyl, pentadecyl, hexadecyl, heptadecyl, and octadecyl, and allyl, undecenyl, oleyl, linoleyl, linolenyl, propenyl, and heptenyl. The active compounds of the inventive compositions may contain straight or branched aliphatic groups. Aromatic radicals are exemplified by phenyl, aniline, or substituted phenyl or aniline groups. Suitable mixed aliphatic aromatic radicals are exemplified by benzyl, phenyl ethyl, phenoxy ethyl, and vinyl benzyl. Cycloaliphatic radicals are exemplified by but not limited to cyclopentyl and cyclohexyl.

Examples of compounds suitable for inclusion in the inventive compositions according to the second embodiment of the invention are set forth below:

3-(N,N-Dibutylamino)-2-hydroxypropyl-$\beta$-D-Galactopyranoside
3-(butylamino)-2-hydroxypropyl-$\beta$-D-Galactopyranoside
3-(pentylamino)-2-hydroxypropyl-$\beta$-D-Galactopyranoside
3-(hexylamino)-2-hydroxypropyl-$\beta$-D-Galactopyranoside
3-(heptylamino)-2-hydroxypropyl-$\beta$-D-Galactopyranoside
3-(octylamino)-2-hydroxypropyl-$\beta$-D-Galactopyranoside
3-(nonylamino)-2-hydroxypropyl-$\beta$-D-Galactopyranoside 3-(decylamino)-2-hydroxypropyl-β-D-Galactopyranoside
3-(dodecylamino)-2-hydroxypropyl-β-D-Galactopyranoside
3-(tetradecylamino)-2-hydroxypropyl-β-D-Galactopyranoside
3-(hexadecylamino)-2-hydroxypropyl-β-D-Galactopyranoside
3-(octadecylamino)-2-hydroxypropyl-β-D-Galactopyranoside
3-(eicosylamino)-2-hydroxypropyl-β-D-Galactopyranoside
3-(docosylamino)-2-hydroxypropyl-β-D-Galactopyranoside
3-(tetracosylamino)-2-hydroxypropyl-β-D-Galactopyranoside
3-(hexenylamino)-2-hydroxypropyl-β-D-Galactopyranoside
3-(decenylamino)-2-hydroxypropyl-β-D-Galactopyranoside
3-(dodecenylamino)-2-hydroxypropyl-β-D-Galactopyranoside
3-(tetradecenylamino)-2-hydroxypropyl-β-D-Galactopyranoside
3-(hexadecenylamino)-2-hydroxypropyl-β-D-Galactopyranoside
3-(octadecenylamino)-2-hydroxypropyl-β-D-Galactopyranoside
3-(docosenylamino)-2-hydroxypropyl-β-D-Galactopyranoside
3-(tetracosenylamino)-2-hydroxypropyl-β-D-Galactopyranoside
3-(3-oxa-tridecylamino)-2-hydroxypropyl-β-D-Galactopyranoside
3-(fluorododecylamino)-2-hydroxypropyl-β-D-Galactopyranoside
3-(butylamino)-2-hydroxypropyl-lactoside
3-(N,N-dimethylamino)-2-hydroxypropyl-lactoside
3-(octylamino)-2-hydroxypropyl-lactoside
3-(dodecylamino)-2-hydroxypropyl-lactoside Compounds of Formula B may be quaternized by treating the compound with alkyl halide (to quarternize) or acid (to protonate). Suitable alkyl halides include, for instance, methyl chloride, and the like. Suitable acids may be organic and inorganic acids and include but are not limited to HCl, H$_2$SO$_4$, and acetic acid. Examples of quaternized compounds of Formula B include but are not limited to:

3-(N,N,N-trimethylammonio)-2-hydroxypropyl-β-D-galactopyranoside, chloride
    3-(N-methyl-N,N-dibutylammonio)-2-hydroxypropyl-β-D-galactopyranoside, chloride In the third embodiment of the invention, oral hygiene compositions according to the invention may include any mixture of compounds having Formula A with compounds having Formula B.

The glyceroglycolipids having Formula A and Formula B suitable for inclusion in the inventive compositions are formed from a precursor having an epoxide group at the location where the ether or the amine linkage is formed and having a sugar (which contains β-D-galactose) group.

The sugar may be protected or unprotected. An example of such a precursor would be the β-D-galactose epoxide compound having the structure:

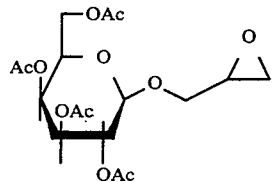

Once the precursor compound is obtained, it can be reacted with an alcohol ROH (wherein R represents the desired chain length of the alkyl group forming the ether linkage) desirably in the presence of a Lewis acid catalyst such as zinc chloride or stannic chloride; or in the presence of a cationic radical generator such as 2,3-Dichloro-5,6-dicyano benzoquinone (DDQ) to form the desired glyceroglycolipid with ether linkage (Formula A). The resulting compound may be further reacted with an appropriate acyl chloride to obtain the glyceroglycolipif of Formula A wherein R$^1$ is not hydrogen.

In order to obtain the desired glyceroglycolipid with an amine linkage (Formula B), once the precursor compound is obtained, it can be reacted with a primary or a secondary amine NHR$^2$R$^3$ (wherein R$^2$ and R$^3$ are as defined above). The amine is added in an inert solvent (e.g. tetrahydrofuran, acetonitrile, dioxane) or neat at room temperature.

The epoxide precursor used to form the desired glyceroglycolipid antiplaque agent can in turn be formed in a variety of ways.

For example, a galactose epoxide compound may be synthesized enzymatically via the hydrolysis of lactose in the presence of allyl alcohol and β-galactosidase to form a β-allyl galactopyranoside which can then be protected and oxidized to the corresponding epoxide with m-chloro-peroxybenzoic (m-CPBA) acid in dichloromethane.

This type of reaction, which is taught in Nilsson, K. G. I., *Carbohydrate Research*, 180:53–59 (1988) is set forth below:

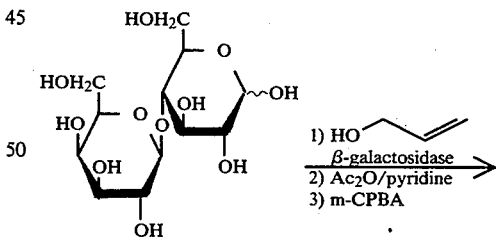

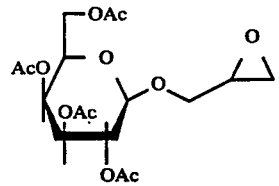

A chemical mode for preparation of the galactose epoxide involves the use of acetobromogalactose (2,3,4,6-tetra-O-acetyl-α-D-galactopyranosyl bromide) mixed with allyl alcohol with mercuric cyanide. This simple Koenigs-Knorr glycosidation affords the β-allyl galactopyranoside tetraacetate in very good yield. Oxidation with peracide gives the protected epoxide sugar.

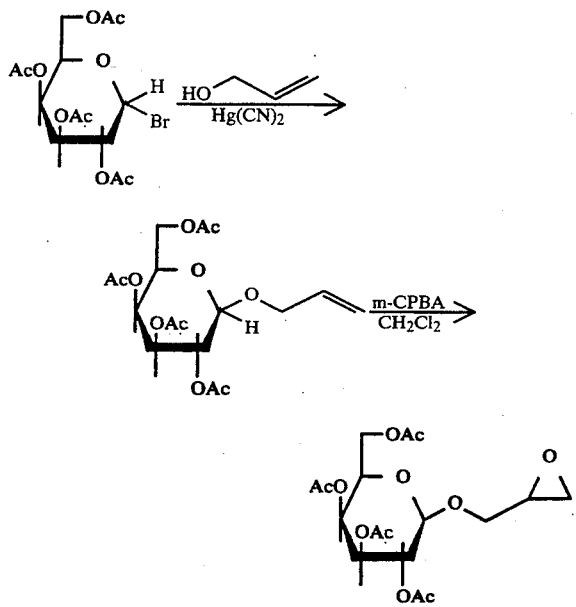

The glyceroglycolipid compounds within the scope of the invention are capable of delivering improved antiplaque benefits by inhibiting bacterial adhesion to a greater degree than that observed for parent saccharides, e.g., β-galactose or lactose.

The glyceroglycolipid compounds are employed in the present invention in an amount effective to inhibit plaque formation. The amount depends on the particular compound employed, but ranges generally from about 0.0001% to about 20%, preferably from about 0.001% to about 10%, and most preferably from about 0.01% to about 5%, by weight of the final composition.

It is also preferred that the amino sugars are water-soluble in order to ease the formulation, particularly of toothpaste and mouthwash compositions, and to increase the diffusibility of the amino sugars into plaque matrix.

The preferred oral compositions of the present invention are in the form of toothpaste, dental cream, gel or tooth powder, as well as mouthwash, pre-brushing rinse, or post-brushing rinse formulations, chewing gums and lozenges.

Ingredients typically included in toothpastes and gels may be used in toothpaste and gel compositions in accordance with the invention. Suitable ingredients include abrasive polishing materials, sudsing agents, flavoring agents, humectants, binders, sweetening agents, and water.

Mouthwashes are typically comprised of a water/alcohol solution, flavor, humectant, sweetener, foaming agent, and colorant.

Abrasives which may be used in the compositions of the invention include alumina and hydrates thereof, such as alpha alumina trihydrate, magnesium trisilicate, magnesium carbonate, aluminosilicates, such as calcined aluminum silicate and aluminum silicate, calcium carbonate, zirconium silicate, polymethyl methacrylate, powdered polyethylene, silica xerogels, hydrogels and aerogels and the like. Also suitable as abrasive agents are calcium pyrophosphate, insoluble sodium metaphosphate, calcium carbonate, dicalcium orthophosphate, particulate hydroxyapatite and the like. Depending on the form which the oral composition is to take, the abrasive may be present in an amount of from 0 to 70% by weight, preferably 1 to 70% by weight, more preferably from 10 to 70% by weight, particularly for toothpastes.

Humectants contemplated for use in the present invention include glycerol, polyol, sorbitol, polyethylene glycols, propylene glycol, hydrogenated partially hydrolyzed polysaccharides and the like. The humectants are generally present in amounts of from 0 to 80%, preferably 5 to 70% by weight, particularly for toothpastes. Thickeners suitable for use in the invention include silica. Thickeners may be present in toothpaste creams and gels at 0.1 to 20% by weight.

Binders suitable for use in the compositions of the invention include hydroxyethyl cellulose (Natrosol ®), sodium carboxymethyl cellulose and hydroxypropyl cellulose (Klucel ®), as well as xanthan gums, Irish moss and gum tragacanth. Binders may be present in the toothpaste of the invention to the extent of from 0.01 to 10%. Sweeteners suitable for use in the present dentifrice, preferably at levels of about 0.1% to 5%, include saccharin.

Suitable foaming agents include soap, anionic, cationic, nonionic, amphoteric and/or zwitterionic surfactants. These may be present at levels of 0 to 15%, preferably 0.1 to 15%, more preferably 0.25 to 10% by weight. It should be noted that many of the glycoside-surface active agents described in the present invention also may be used as foaming agents at concentrations ranging from 0 to 15% by weight.

Certain pyrophosphate and other polyphosphate salts have been disclosed in U.S. Pat. Nos. 4,515,772 and 4,627,977 as being useful as anti-calculus agents. These include di- and tetra-alkali metal pyrophosphates wherein the alkali metals are preferably selected from the group consisting of sodium and potassium. Polyphosphate salts may be included generally in the amount such that it provides for at least 0.5% polyphosphate anions, the upper level being about 10%, preferably about 7.5%.

Various anionic polymers may be employed as anticalculus and/or antiplaque agents. Suitable polymers include carboxylate polymers, sulfonate polymers, polymers containing a sulfonate and a carboxylate moiety, carboxylate polymers containing phosphinate units, and mixtures thereof. The carboxylate polymers suitable in the present compositions are described by Gaffar et al., U.S. Pat. No. 4,808,400, incorporated by reference herein. Suitable carboxylate polymers containing mono- or disubstituted hypophosphite units along the polymer backbone are described in a U.S. Pat. No. 5,011,682 incorporated by reference herein. The anionic polymers may be included at a level from about 0.01 to about 10%, preferably from about 0.05 to about 5%.

Zinc salts are disclosed as anti-calculus and anti-plaque agents in U.S. Pat. No. 4,100,269 and in U.S. Pat. Nos. 4,416,867, 4,425,325 and 4,339,432. Preferred compositions of the invention include zinc salts, particularly zinc citrate. The zinc compounds may be present in the compositions in amounts sufficient to furnish about 0.01% to about 4% zinc, or preferably about 0.05% to about 1%, zinc ion.

Fluoride sources used in toothpastes such as sodium fluoride, stannous fluoride, sodium monofluorophosphate, zinc ammonium fluoride, tin ammonium fluoride, calcium fluoride and cobalt ammonium fluoride may be, and preferably are, included for delivering anti-caries benefit. Preferred compositions of the invention include the fluoride source. Fluoride ions are typically provided at a level of from 0 to 1500 ppm, preferably 50 to 1500 ppm, although higher levels up to about 3000 ppm may be used.

Flavors are usually included in toothpastes in low amounts, such as from 0.01 to about 5% by weight, especially from 0.1% to 5%.

Water-soluble antibacterial agents, such as chlorhexidine digluconate, hexetidine, alexidine, quaternary ammonium anti-bacterial compounds and water-soluble sources of certain metal ions such as zinc, copper, silver and stannous (e.g., zinc, copper and stannous chloride, and silver nitrate) may also be included.

Titanium dioxide is a suitable whitener.

Dyes/colorants suitable for dentifrices, i.e., FD&C Blue #1, FD&C Yellow #10, FD&C Red #40, etc., may be employed in the dentifrices of the invention.

Various other optional ingredients may be included in the compositions of the invention, such as preservatives, vitamins such as vitamin C and E, other antiplaque agents such as stannous salts, copper salts, strontium salts and magnesium salts. Also included may be pH adjusting agents, anti-caries agents such as urea, calcium glycerophosphate, sodium trimetaphosphate, silicone polymers, plant extracts, desensitizing agents for sensitive teeth such as potassium nitrate and potassium citrate, and mixtures thereof.

Casein and/or its hydrolysate may be included as anticariess agents, e.g. at a level of 0.01 to 20% by weight, preferably 0.1 to 10%.

The corresponding compounds mentioned above which are used in toothpastes, are generally suitable within the ranges above for mouthwashes as well. The mouthwash can include ethanol at a level of from 0 to 60%, preferably from 5 to 30% by weight.

The inventive compositions may constitute an integral part of a toothpaste cream or gel, or mouthwash and applied during the regular brushing, or the compositions may be formulated and packaged as a separate treatment and applied separately before, after, and/or in between regular brushing times. The compositions may be applied by brushing, rinsing, chewing, etc.

The following specific examples further illustrate the present invention, but the invention is not limited thereto.

EXAMPLE 1

Various glyceroglycolipids suitable for use in the present invention were synthesized as follows:

Synthesis of 3-(N,N-dibutylamino)-2-hydroxypropyl-$\beta$-D-galactopyranoside

Acetobromogalactose (2,3,4,6-tetra-O-acetyl-$\alpha$-D-galactopyranosyl bromide) was mixed with allyl alcohol and mercuric cyanide via the Koenigs-Knorr glycosylation to obtain allyl $\beta$-D-galactopyranoside tetraacetate. This was followed by oxidation with 3-chloroperoxybenzoic acid in dichloromethane to obtain 2,3-epoxypropyl-$\beta$-D-galactopyranoside, 2,3,4,6-0-tetracetate.

In a 35 ml two neck flask was added 0.32 g (0.8 mmoles) of the above identified epoxide compound and 1.5 ml of dry acetonitrile, followed by addition of N,N-dibutylamine (0.2 g, 1.6 mmoles). The reaction was allowed to run at room temperature and was followed by thin layer chromotography using a 9:1 CHCl$_3$:MeOH with a drop of ammonium hydroxide as eluent. Rf value of the new product was found to be 0.36 (the Rf of starting epoxide prior to consumption had been 0.80).

Column chromatography was used to separate the ring-opened adduct from the excess amine using a 9:1 CHCl$_3$:MeOH with a drop of ammonium hydroxide as eluent. Total yield of this syrupy ring-opened product was 0.40 g. The product was confirmed by NMR and mass spectroscopy.

The product was further deprotected using catalytic amounts of sodium methoxide in 20 ml of anhydrous methanol. TLC (Thin layer chromatography) showed that after 8 hours the product was completely deacetylated. The deacylated product was passed through a short silica gel column (8:2 CHCl$_2$:methanol) to yield 0.175 g of the final product, 3-(N,N-dibutylamino)-2-hydroxypropyl-$\beta$-D-galacropyranoside.

Synthesis of 3-(octyloxy)-2-hyroxypropyl-$\beta$-D-galactopyranoside

Acetobromogalactose (2,3,4,6-tetra-O-acetyl-$\beta$-D-galactopyranosyl bromide) was mixed with allyl alcohol and mercuric cyanide via the Koenigs-Knorr glycosylation to obtain allyl-$\beta$-D-galactopyranoside tetraacetate. This was followed by oxidation with 3-chloroperoxybenzoic acid in dichloromethane to obtain 2,3-epoxypropyl-$\beta$-D-galactopyranoside 2,3,4,6-0-tetracetate (epoxide compound). To a solution of the above-identified epoxide compound (0.50 g, 1.24 mmoles) and 1-octanol (5–6ml) was added 0.045 g of DDQ (2,3-dichloro-5,6-dicyano-1,4-benzoquinone). The reaction was run at 60°–70° C. under an inert atmosphere of nitrogen. Reaction was followed by thin layer chromatography in an eluent of 50/50 volume of ethyl acetate/hexane. The product had a Rf value of 0.6. After one day another 0.06 g of DDQ was added to the mixture. When the reaction was complete, the product (0.35 g) was isolated by column chromatography on 60 Å (Merck) silica gel in a solvent system consisting of 50% ethyl acetate/50% hexane.

Deprotection was done using sodium methoxide in 35 ml of anhydrous methanol for 5–6 hours. Methanol was removed under reduced pressure. The crude product was further purified on a silica gel column (9:1 CHCl$_3$, MeOH) to give the final product as a white solid (0.15 g) as seen below:

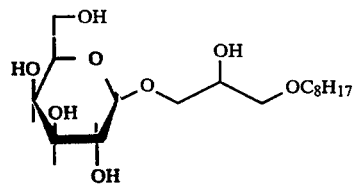

Alternative Synthesis of 3-(octyloxy)-2-hydroxypropyl-$\beta$-D-galactopyranoside:

In a 25 ml two neck round bottom flask was added 0.80 g (1.98 mmoles) of 2,3-epoxypropyl-$\beta$-D-galactopyranoside 2,3,4,6-0-tetraacetate and 4.0 equivalents of 1-octanol. The reaction mixture was cooled to $-10°$ C. followed by addition of 0.034 equivalent of a 1.0M solution of SnCl$_4$ in dichloromethane. The reaction was allowed to warm up to room temperature over a period of one hour, and then heated to a temperature of 45° C. for 12–14 hours. Column chromatography was used to purify the product. The excess octanol was initially isolated using a 9:1 hexane/ethyl acetate eluent. Subsequent elution with 1:1 hexane/ethyl acetate gave 0.55 g of a clear syrupy material (52% yield). $^1$H NMR and massspectroscopy showed identical spectra to the DDQ reaction product. Deprotection (same as Example 1) gave 0.36 g (95% yield) of final product.

EXAMPLE 2

Antiplaque agents within the scope of the invention prepared in Example 1 were tested for their ability to inhibit coaggregation between *A. naeslundii* and *S. sanguis*.

BACTERIAL COAGGREGATION ASSAY

A bacterial coaggregation assay was used to determine the ability of various antiplaque agents to interfere with lectin-mediated binding among various bacterial species. For instance, many *Actinomyces naeslundii* strains coaggregate with *Streptococcus sanguis* as a result of binding between a lectin produced by the *A. naeslundii* cells and β-D-galactose-containing structures on the surface of the streptococci. For the present assay, *A. naeslundii* PK29 and *S. sanguis* G9B were cultured overnight in a medium containing 2.5% tryptone, 1.5% yeast extract, 0.1% magnesium sulfate, and 1.0% fructose. The cells were then washed twice in a 1.0 mM potassium phosphate buffer (pH=6.8) containing 1.0 mM calcium chloride, 0.1 mM magnesium chloride, and 50.0 mM potassium chloride (buffered KCl ), after which they were resuspended in buffered KCl at an optical density (540 nm) of 1.5. The coaggregations were performed by combining 0.5 ml of each bacterial suspension with 0.2 ml of 5.0% bovine serum albumin (BSA) and 0.8 ml of an appropriate concentration of a targeted anti-plaque agent in 3.0 ml capped polystyrene cuvettes. The cuvettes (path length 1 cm) were gently inverted at room temperature, and the optical density (540 nm) was determined as a function of time (2.0 min intervals; for 20 min). The instrument employed to measure OD was Gilson Response ® Spectrophotometer (bought from Gilson).

A "relative potency" value was assigned to the tested compounds by calculating the difference in the optical density change resulting from inclusion of the targeted antiplaque agent in the coaggregation assay, and dividing by the difference in the optical density change resulting from inclusion of the parent saccharide.

The results that were obtained are summarized in Table 1.

TABLE 1

| Glycoside | Relative Potency |
|---|---|
| Galactose | 1.0 |
| 3-(octyloxy)-2-hydroxypropyl-β-D-galactopyranoside | 1.7 |
| 3-(N,N-Dibutylamino)-2-hydroxypropyl-β-D-galactopyranoside | 4.0–5.0 |

Unexpectedly, glyceroglycolipids within the scope of the invention exhibited much greater inhibitory activity than the inhibitory activity of the starting saccharide, galactose. As shown in Table 1, relative to galactose, antiplaque agents within the scope of the invention were approximately 2–5 fold more potent as inhibitors of β-galactose specific coaggregation between *A. naeslundii* PK29 and *S. sanguis* G9B.

EXAMPLE 3

ANTIMICROBIAL ACTIVITY DETERMINATION

The antimicrobial activity of the targeted agents was assessed by determining the minimum inhibitory concentration (MIC). Pure cultures of various strains of oral bacterial species as indicated in Table 2 were combined with serial dilutions of the targeted agents in beef heart infusion broth (BHI); starting bacterial concentrations were approximately $1.0 \times 10E6$ colony forming units (CFU) per ml. The mixtures were incubated aerobically at 37 degrees C. and the optical density (540 nm, path length 1 cm) of the cultures was measured at 0.0, 24.0 and 48.0 hr using Bausch and Lomb Spec 20 variable wavelength spectrophotometer.

TABLE 2

| | Minimimum Inhibitory Concentrations (% w/v) | | |
|---|---|---|---|
| Compound Tested | *Streptococcus sanguis* | *Actinomyces naeslundii* | *Neisseria subflava* |
| Sodium dodecyl sulfate | 0.0015 | 0.0008 | 0.0008 |
| 3-(octyloxy)-2 hydroxypropyl-β-D-galactopyranoside | >0.05 | >0.05 | >0.05 |
| 3-(dodecyloxy)-2 hydroxypropyl-β-D-galactopyranoside | 0.0125 | 0.0125 | 0.0125 |
| methyl lactoside | >0.05 | >0.05 | >0.05 |

As can be seen from Table 2, compounds of Formula A within the scope of the invention which have R and/or R1 containing more than 8 carbon atoms exhibited substantial antimicrobial activity; such compounds preferably contain from 10 to 16 carbon atoms. Likewise, it is expected that amine linked glyceroglycolipids of Formula B which have surfactant activity will also exhibit antimicrobial activity. Compounds of Formula B which have been quaternized are expected to have substantial antimicrobial activity.

EXAMPLE 4

Several groups of the antiplaque compounds employed in the inventive composition, for instance compounds of Formula A having R and/or $R^1$ containing 8 or more carbon atoms, and compounds of Formula B having $R^2$ and/or $R^3$ containing 8 or more carbon havings and at least one of $R^2$, $R^3$, $R^5$, or $R^6$ is a hydrocarbon radical. The surfactant properties of various glyceroglycolipids have been described in greater detail in co-pending applications (attorney docket No. 91-0099-EDG and 91-0128-EDG), examples of those applications demonstrating the surfactant properties of the glyceroglycolipids included in the present invention are as follows:

Critical Micelle Concentration (CMC)

The CMC is defined as the concentration of a surfactant at which it begins to form micelles in solution. Specifically, materials that contain both a hydrophobic group and a hydrophilic group (such as surfactants) will tend to distort the structure of the solvent (i.e., water) they are in and therefore increase the free energy of the system. They therefore concentrate at the surface, where, by orienting so that their hydrophobic groups are directed away from the solvent, the free energy of the solution is minimized. Another means of minimizing the free energy can be achieved by the aggregation of these surface-active molecules into clusters or micelles with their hydrophobic groups directed toward the interior of the cluster and their hydrophilic groups directed toward the solvent.

The value of the CMC is determined by surface tension measurements using the Wilhemy plate method. While not wishing to be bound by theory, it is believed that a low CMC is a measure of surface activity (i.e., lower CMC of one surfactant versus another indicates the surfactant with lower CMC is more surface active). In this regard, it is believed that lower CMC signifies that lesser amounts of a surfactant are required to provide the same surfactancy benefits as a surfactant with higher CMC.

The CMC of 3-(dodecyloxy)-2-hydroxypropyl-$\beta$-D-galactopyranoside was measured at $1.23 \times 10^{-4}$M at 25° C. The CMC of n-$C_{12}$ alcohol with 7 ethoxylated units (from Neodol ™ surfactants ex Shell) is $7.3 \times 10^{-5}$M [40° C.]. This indicates that some glyceroglycolipids included in the invention are comparable to well-known commercially available surfactants.

Krafft Points

The temperature at and above which surfactants begin to form micelles is referred to as Krafft point (Tk) and at this temperature the solubility of a surfactant becomes equal to its CMC.

Krafft point was measured by preparing a 1% dispersion of the surfactant in water. If the surfactant was soluble at room temperature, the solution was cooled to 0° C. When the surfactant did not precipitate out, its Krafft point was considered to be <0° C. If it precipitated out, the solution was slowly warmed with stirring in a water bath. The temperature at which the precipitate dissolved was determined to be the Krafft point.

If the Krafft point was above room temperature, the solution was first heated rapidly to dissolve all the surfactant. It was then cooled until precipitation occurred, and was then slowly warmed to determine the Krafft point described above.

While not wishing to be bound by theory, it is believed that lower Krafft points are indicative of a surfactant being more soluble in aqueous system. Also, since micelles exist only at temperature above Tk, surfactants with high Tk will show lower activity at low temperatures. Finally, it is believed that surfactants with lower Krafft points are easier to formulate in multi-electrolyte systems because of their greater tolerance to salt.

The Krafft point of 3-(dodecyloxy)-2-hydroxypropyl-$\beta$-D-galactopyranoside has been measured at about less than 8° C. This Krafft point is another good indication of surfactant activity.

Foam Height

Since most of the foaming data on surfactants is typically obtained by the Ross-Miles method (Ross, J. and Miles, G. D., Am. Soc. for Testing Material Method D1173-53 Philadelphia, Pa. [1953]; Oil & Soap [1958] 62:1260) the foaming ability of these surfactants was also acquired using this method.

In the Ross-Miles method, 200 mL of a solution of surfactant contained in a pipette of specified dimensions with a 2.9-mm-i.d. orifice is allowed to fall 90 cm onto 50 mL of the same solution contained in a cylindrical vessel maintained at a given temperature by means of a water jacket. The height of the foam produced in the cylindrical vessel is read immediately after all the solution has run out of the pipette (initial foam height) and then again after a given amount of time.

Using this method, the foam production (measured initially) and foam stability (the height after 10 minutes) are reported. All of the foaming was achieved at 45° C. in water with 120 ppm hardness. The foam height is represented in millimeters (mm).

The initial foam height and height after 10 minutes (i.e. foam stability) was measured for 3-(dodecyloxyl)-2-hydroxypropyl-$\beta$-D-galactopyranoside (DHG) and for a common surfactant, sodium dodecyl sulfonate (SDS) and results set forth below:

|  | Initial Height | After 10 Minutes |
|---|---|---|
| DHG | 135 | 124 |
| SDS | 153 | 144 |

As seen from this data, the foaming ability of DHG is comparable to that of other well-known, commercially available surfactants.

Oral hygiene compositions including $\beta$-galactose-containing glyceroglycolipids which also function as surfactants are preferred according to the present invention due to their dual benefit: the ability to inhibit bacterial adhesive interactions and their ability to disperse bacteria.

EXAMPLE 5

A typical toothpaste formula containing a glyceroglylcolipid antiplaque plaque inhibitor of the present invention is as follows:

| Toothpaste Formula (pH = 5-9) | |
|---|---|
| Component | Percent by Weight of the Final Composition |
| 70% Sorbitol | 64.0% |
| Abrasive Silica | 10.0% |
| Thickening Silica | 9.0% |
| Glyceroglycolipid Antiplaque Agent | 5.0% |
| Antiplaque Agent | 5.0% |
| Polyethylene Glycol | 5.0% |
| Sodium Dodecyl Sulfate | 1.5% |
| Flavor | 1.0% |
| Sodium Saccharinate | 0.3% |
| Sodium Fluoride | 0.24% |
| Preservative (Benzoate) | 0.08% |
| Dye | <.01% |
| Sodium Carboxymethyl Cellulose | 0.15% |
| Water | to 100% |

EXAMPLE 6

A typical formula for a mouthwash containing the glyceroglycolipid antiplaque agents of the present invention is as follows:

| Mouthwash Formula (pH = 6.5) | |
|---|---|
| Component | Percent by Weight of Final Composition |
| Ethanol | 12.5% |
| 70% Sorbitol | 7.0% |
| Glyceroglycolipid Antiplaque Agent | 5.0% |
| Tween 20 | 0.55% |
| Preservatives (parabens) | 0.2% |
| Flavor | 0.1% |
| Dye | <.1% |
| Sodium Saccharinate | 0.65% |
| Sodium Chloride | 0.05% |
| Sodium Acetate | 0.015% |

-continued

| Mouthwash Formula (pH = 6.5) | |
|---|---|
| Component | Percent by Weight of Final Composition |
| Acetic Acid | 0.015% |
| Water | to 100% |

Some suppliers for the materials employed in the invention have been mentioned in the description. Other materials in the description of the invention are available from the following suppliers:

| Material | Supplier |
|---|---|
| Acetobromogalactose (2,3,4,6-Tetra-O-acetyl-alpha-D-galactopyranosyl bromide) | Aldrich |
| Allyl alcohol | Aldrich |
| Mercury(II) cyanide | Aldrich |
| DDQ (2,3-Dichloro-5,6-dicyano-1,4-benzoquinone) | Aldrich |
| 3-Chloroperoxybenzoic acid | Aldrich |
| β-Galactosidase (Grade VIII) from *E. Coli* | Sigma |
| Tin (IV) chloride (1.0M solution in dichloromethane) | Aldrich |
| Dibutylamine | Aldrich |
| Alpha-D-lactose monohydrate | Fisher |
| 1-Octanol (octyl alcohol) | Aldrich |
| 1-Dodecanol (dodecyl alcohol) | Aldrich |
| 1-Hexadecanol (cetyl alcohol) | Aldrich |
| Bacteria: | |
| a) *Streptococcus sangius* G9B | In-house culture collection |
| b) *Actinomyces naeslundii* PK29 | Paul Kollenbrander, NIH, Bethes |
| c) *Neisseria subflava* A1078 | Phil Marsh, PHLS (centre for Applied Microbiology, Porton Down, UK |
| Lactose | BBL - Becton Dickinson |
| Galactose | Fisher |
| Bovine Serum Albumin | Sigma |
| Tween 20$^R$ (polysorbate 20) | ICI Americas Inc. |
| Plastic cuvettes - 4–5 ml polystyrene | Disposlab Kartell |
| Tryptone | Difco |
| Yeast Extract | BBL - Becton Dickinson |
| Beef Heart Infusion Broth | BBL - Becton Dickinson |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. An oral hygiene antiplaque composition comprising a suitable carrier and an effective antiplaque amount of at least one compound selected from the group consisting of:

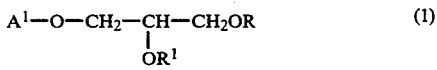  (1)

wherein $A^1$ is a saccharide comprising at least one β-D-galactose group as a sugar moiety recognized by lectins on oral bacteria and wherein R and $R^1$ are the same or different and are selected from the group consisting of hydrogen, an aliphatic hydrocarbon radical, an aromatic radical, a cycloaliphatic radical, and an acyl group, except that R and $R^1$ cannot both be hydrogen at the same time; and

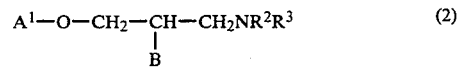  (2)

wherein $R^2$ and $R^3$ are the same or different and are selected from the group consisting of hydrogen, an aliphatic hydrocarbon radical, an aromatic radical, and a cycloaliphatic radical and wherein B is OH or a $NR^5R^6$ group wherein $R^5$ and $R^6$ are the same or different and are selected from the group consisting of hydrogen, an aliphatic hydrocarbon radical, an aromatic radical, and a cycloaliphatic radical, wherein B and $NR^2R^3$ are positionally interchangeable.

2. The composition of claim 1 wherein at least one of $R^2$, $R^3$, $R^5$, or $R^6$ is a hydrocarbon radical having from 1 to 36 carbon atoms.

3. The composition of claim 1 wherein R and $R^1$ are the same or different and both together contain from 1 to 36 carbon atoms.

4. The composition of claim 1 wherein $A^1$ is β-D-galactose.

5. The composition of claim 1 wherein $A^1$ is lactose.

6. The composition of claim 1 wherein $A^1$ is β-D-galactose, $R^1$ is hydrogen and R is a straight chain hydrocarbon radical having from 6 to 18 carbon atoms.

7. The composition of claim 1 wherein $R^2$ and $R^3$ are the same or different and both together contain from 1 to 36 carbon atoms.

8. The composition according to claim 1 wherein $R^2$ is hydrogen and $R^3$ is a hydrocarbon radical having 6 to 18 carbon atoms and B is OH.

9. The composition of claim 8 wherein $A^1$ is β-D-galactose.

10. The composition of claim 8 wherein $A^1$ is lactose.

11. The composition of claim 1 wherein the composition further comprises a source of zinc ion.

12. The composition of claim 1 wherein the composition further comprises a source of fluoride ion.

13. The composition of claim 1 wherein the amount of the compound is in the range of from 0.0001 to 20%.

14. The composition of claim 1 wherein the compound is quaternized.

15. The composition of claim 1, wherein the compound is present in the amount effective to inhibit bacterial adhesive interactions.

16. A method of inhibiting bacterial aggregation in an oral cavity comprising applying into said oral cavity an oral hygiene antiplaque composition comprising a suitable carrier and an effective plaque-inhibiting amount of at least one compound selected from the group consisting of:

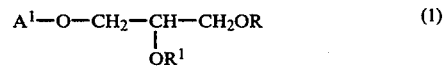  (1)

wherein $A^1$ is a saccharide comprising β-D-galactose as a sugar moiety recognized by lectins on oral bacteria and wherein R and $R^1$ are the same or different and are selected from the group consisting of hydrogen, an aliphatic hydrocarbon radical, an aromatic radical, a cycloaliphatic radical, and an acyl group, except that R and $R^1$ cannot both be hydrogen at the same time; and

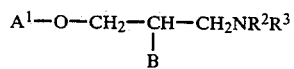

(2)

wherein $R^2$ and $R^3$ are the same or different and are selected from the group consisting of hydrogen, an aliphatic hydrocarbon radical, an aromatic radical, and a cycloaliphatic radical and wherein B is OH or a $NR^5R^6$ group wherein $R^5$ and $R^6$ are the same or different and are selected from the group consisting of hydrogen, an aliphatic hydrocarbon radical, an aromatic radical, and a cycloaliphatic radical, wherein B and $NR^2R^3$ are positionally interchangeable.

* * * * *